United States Patent [19]

Moberg

[11] Patent Number: 4,715,381
[45] Date of Patent: Dec. 29, 1987

[54] BATTERY TEST CIRCUIT FOR A HEART PACEMAKER

[75] Inventor: Lennart Moberg, Spanga, Sweden

[73] Assignee: Siemens Aktiengesellschaft, Berlin and Munich, Fed. Rep. of Germany

[21] Appl. No.: 908,212

[22] Filed: Sep. 17, 1986

[30] Foreign Application Priority Data

Oct. 2, 1985 [DE] Fed. Rep. of Germany ....... 3535202

[51] Int. Cl.⁴ .................... A61N 1/00; H05G 0/00; A61B 5/04
[52] U.S. Cl. .................. 128/419 PT; 128/419 PG; 128/419 PS; 128/697
[58] Field of Search ................ 128/419 PT, 419 PS, 128/419 PG, 697

[56] References Cited

U.S. PATENT DOCUMENTS

| | | | |
|---|---|---|---|
| 3,841,336 | 10/1974 | Daynard | 128/419 PT |
| 4,102,346 | 7/1978 | Fulker | 128/419 PT |
| 4,276,883 | 7/1981 | McDonald et al. | 128/419 PT |
| 4,445,512 | 5/1984 | Krupka et al. | 128/419 PT |
| 4,527,567 | 7/1985 | Fischler et al. | 128/419 PG |
| 4,556,061 | 12/1985 | Barreras et al. | 128/419 PT |

Primary Examiner—William E. Kamm
Assistant Examiner—Timothy Keegan
Attorney, Agent, or Firm—Hill, Van Santen, Steadman & Simpson

[57] ABSTRACT

A battery test circuit for a heart pacemaker has a stimulation pulse counter and input logic which identify the consumed charge from the operating values of the pacemaker, from the number of stimulation pulses emitted, and from a time-dependent base value. The consumed charge identified in each test is summed in a charge counter. The content of the charge counter is accordingly a measure for the total charge consumed.

5 Claims, 7 Drawing Figures

BATTERY TEST CIRCUIT FOR A HEART PACEMAKER

RELATED APPLICATION

The subject matter of this application is related to the subject matter of the co-pending application of Lennart Moberg entitled "Battery Test Circuit For A Heart Pacemaker" filed simultaneously herewith and identified with attorneys' Ser. No. 06/908,213 filed 9/17/86.

BACKGROUND OF THE INVENTION

The present invention relates to heart pacemakers, and in particular to a circuit for testing the remaining battery life of the battery in a heart pacemaker.

In the use of implantable heart pacemakers, it is important to be able to identify the remaining useful life of the battery, and thus of the heart pacemaker, in a simple manner. It is known to provide a heart pacemaker with circuitry which measures the internal resistance of the battery, thus giving an indication as to the remaining life. For this purpose, the pacemaker is switched to a "test mode." The status of the battery is indicated by generating a series of test pulses at a frequency corresponding to the battery resistance, the frequency being measured externally.

A battery testing unit for a heart pacemaker having a LiI cell is known, wherein the battery is loaded with a known value and the resulting voltage drop is measured. Depending upon the voltage drop, and thus upon the internal resistance of the battery, the stimulation frequency is changed during the test mode, and the stimulation frequency is then externally measured. A test unit of this type, however, is suitable only for a battery having an internal resistance which increases as the battery discharges.

It is an object of the present invention to provide a test circuit for the charge status of the battery of a heart pacemaker which is suited for batteries having a constant internal resistance during at least a portion of their useful life.

The above object is achieved in accordance with the principles of the present invention by a circuit including a stimulation pulse counter and input logic which identify the consumed charge from the pacemaker operating values, from the number of stimulation pulses emitted, and from a chronological base value. The pulse counter and input logic are connected to a memory or charge counter in which the charge which has been consumed since a preceding test is summed. Identification of the charge status of the battery thus does not occur by means of a load connected to the battery, but instead by measuring the charge drawn from the battery, added to a base value, which is summed in a memory. The content of the memory thus provides information regarding the remaining useful life of the battery. The circuit is suitable for all types of batteries, and specifically for batteries having an internal resistance which remains constant over a relatively long period despite discharging of the battery.

The circuit can be constructed as an implantable unit and internally executes all calculations and need only have means for externally reporting a final value which corresponds to the charge status of the battery. It is also possible, however, to undertake the necessary calculations in an external programming device which communicates with an implanted unit which simply acquires the values necessary to make the calculations. The programming device updates the values in ause register in the implantable unit.

Display of the charge status of the battery can be undertaken such that an electrical signal corresponding to the charge status controls a pulse generator which generates at least one marking pulse at the output of the heart pacemaker, the marking pulse having a chronological position with respect to the stimulation pulses which is dependent upon the charge status of the battery. Measurement of the charge status and thus of the remaining useful life of the battery is thus possible by observing the output pulses of the heart pacemaker, and has the additional advantage that the frequency of the stimulation pulses need not be altered during a test mode.

DESCRIPTION OF THE PREFERRED EMBODIMENTS

Figure 1:
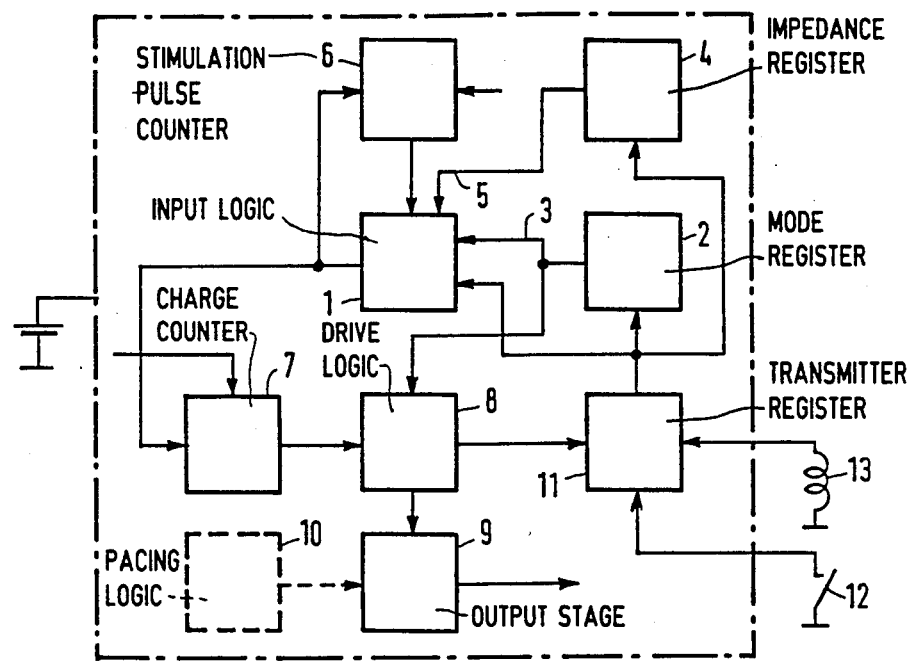
FIG. 1 is a schematic block diagram of a battery status test circuit for a heart pacemaker constructed in accordance with the principles of the present invention.

The basic components of one embodiment of a battery charge status test circuit constructed in accordance with the principles of the present invention are shown in FIG. 1. A signal corresponding to the set therapeutic values of the heart pacemaker is supplied to input logic 1 at an input 3 from a mode register 2. An impedance register 4 supplies a signal to the input logic 1 corresponding to the electrode impedance at another input 5. The number of stimulation pulses generated since a last battery status test are counted in a stimulation pulse counter 6. A charge counter 7 stores an electrical signal corresponding to the charge status of the battery, this electrical signal driving an output stage 9 via drive logic 8. The output stage 9 is connected to the pacing logic 10. The circuit is driven by a transmitter/receiver 11. The trasmitter/receiver 11 can be actuated by a magnetically actuatable contact 12, or can be actuated wirelessly by a coil 13. Signals are supplied to the contact 12 or the coil 13 by an external transmitter/receiver.

When the circuit of FIG. 1 is activated (i.e., placed in the test mode) by a signal supplied through the transmitter/receiver 11, the therapeutic values of the heart pacemaker, such as pulse amplitude, pulse duration and stimulation frequency, are supplied to the input logic 1. Using these signals, the electrode impedance signal, and information regarding basis patient consumption, the input logic 1 calculates the charge which has been comsumed which may be expressed, for example, in basic units of 5μAh. The stimulation pulses which have incremented since the last test, and which the stimulation pulse counter 6 supplies to the input logic 1, are also taken into consideration for this calculation. The consumed charge is summed in the charge counter 7. The content of the charge counter 7, therefore, is a measure of the charge consumed. This signal is mixed into the output signal of the heart pacemaker via the drive logic 8 and the output stage 9, as described in greater detail below.

Figure 2:
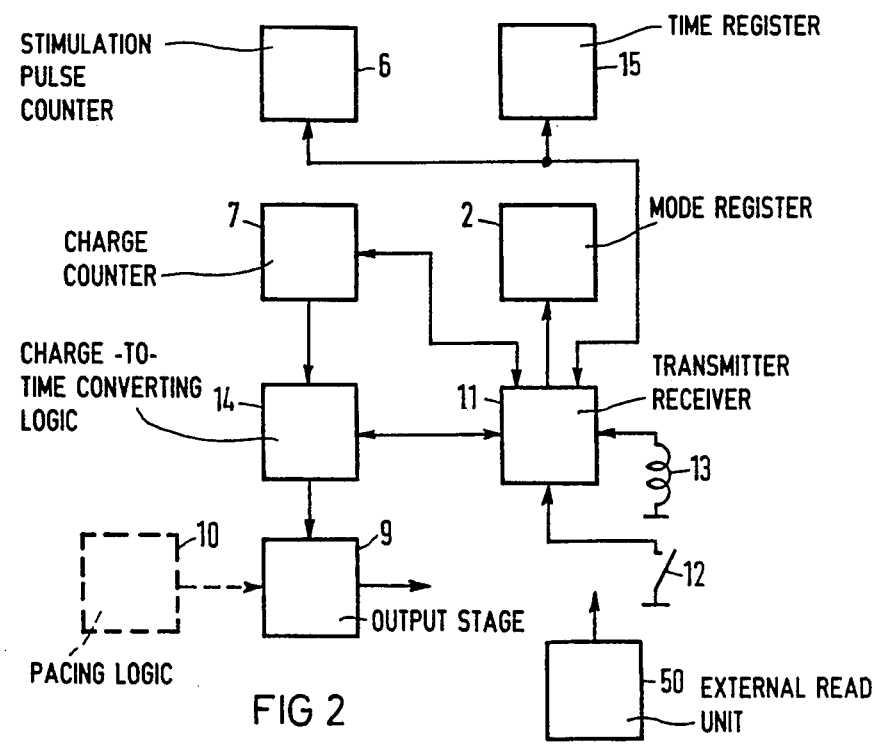
FIG. 2 is a further embodiment of the battery test status circuit constructed in accordance with the principles of the present invention.

In the embodiment of FIG. 2, components identical to those described above are provided with the same reference symbol. In addition to the components of FIG. 1, the embodiment of FIG. 2 includes a time register 15, charge-to-time converting logic 14. The mode register 2, the stimulation pulse counter 6, and the charge counter 7 are interconnected differently from the embodiment in FIG. 1. In the embodiment of FIG. 2, during a test mode, an external read unit 50 first reads the time register 15. The time register 15 then supplies an electrical signal corresponding to the time of the measurement at a predetermined period of, for example, 2 hours. This means that the time register 15 generates a new signal every 2 hours.

With the knowledge of the time of the measurement, the external read unit 50 can identify the fundamental battery consumption. After making this calculation, the external unit 50 reads the current value of the stimulation pulse counter 6, which constitutes the number of stimulation pulses since the last battery test. If the stimulation pulse counter 6 has a current value of zero, it is known that the charge counter 7 is charged only with the fundamental consumption.

If the stimulation pulse counter 6 has a current value differing from zero, the external unit 50 executes the following steps. First, registers for the pulse amplitude, pulse duration and stimulation frequency (not shown) are read. The external unit 50 then calculates the electrode impedance. With these values, the external unit 50 can calculate the charge consumption of each stimulation pulse by a table. This consumption is multiplied by the number of stimulation pulses in the current reading of the stimulation pulse counter 6, and is added to the fundamental consumption. Subsequently, the charge counter 7 is charged with this value and the stimulation pulse counter 6 is reset to zero.

Each time the pacemaker is re-programmed in a manner which influences the consumption, a battery test is undertaken For forming an electrical signal corresponding to the remaining battery capacity, the charge-to-time coverting logic 14 converts the value of the charge counter 7 into a signal corresponding to the remaining battery life. This time can be read via the transmitter/receiver 11, however, it is also possible to mix the signal with the normal pacemaker output signal in the output stage 9 as described below.

The logic 14, which is charge-to-time converting logic, may also be a microprocessor, or can be hardware logic. Another possibility for the logic 14 is a read only memory, the read only memory having a table which converts charge to time. For example, at the beginning of life (BOL) of a new battery, a low value will be selected from the table, which causes a short distance between the stimulation pulse and the marking pulse in the output format of the type shown in FIG. 3.

Figure 3:
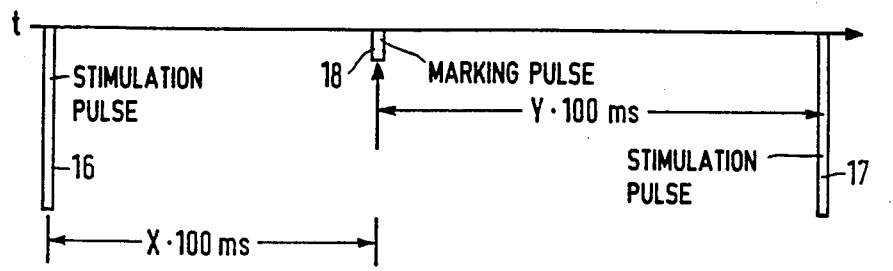
FIG. 3 is one type of output display indicating battery charge status in accordance with the principles of the present invention.

One manner of displaying the battery status signal is shown in FIG. 3. In this embodiment, two successive stimulation pulses 16 and 17 of the pacemaker are shown, with a marking pulse 18 mixed therewith. The marking pulse 18 is generated by the output stage 9. The chronological spacing of the marking pulse 18 from the stimulation pulse 16 depends upon the residual capacity of the battery still remaining and, as shown in FIG. 3, amounts to x times 100 ms or y times 100 ms. Either one of the values x or y corresponds to the remaining battery capacity in years. The marking pulse 18 is mixed with the stimulation pulse signal only in the test mode. During this time, the pacemaker operates with a fixed frequency.

Figure 4:
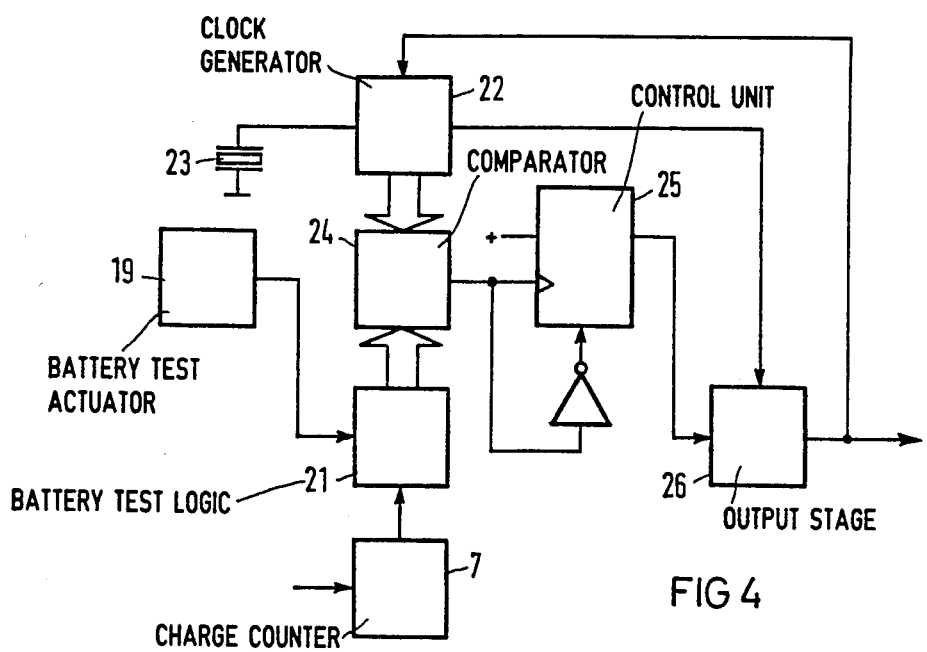
FIG. 4 is a schematic block diagram of a circuit for generating the output sequence shown in FIG. 3.

Circuitry for generating the sequence shown in FIG. 3 is schematically represented in FIG. 4. This circuitry includes a battery test actuator 19 which drives battery test logic 21. The battery test logic 21 is supplied with the contents of the charge counter 7. The value from the charge counter 7 is converted in the battery test logic 21 into a time value, which corresponds to the remaining battery capacity in years (x or y). The value x or y is converted to a distance for the marking pulse 18 from the stimulation pulse 16 or the stimulation pulse 17, which amounts to x or y times 100 ms. The value in the battery test logic 21 is compared in a comparator 24 with a time base which is supplied by a clock generator 22 connected to an oscillator 23. The result of the comparison determines the correct position of the marking pulse 18 with respect to the stimulation pulse 16 or 17, and the marking pulse is mixed with the output pulses of the pacemaker via a control stage 25 and an output stage 26.

Figure 5:
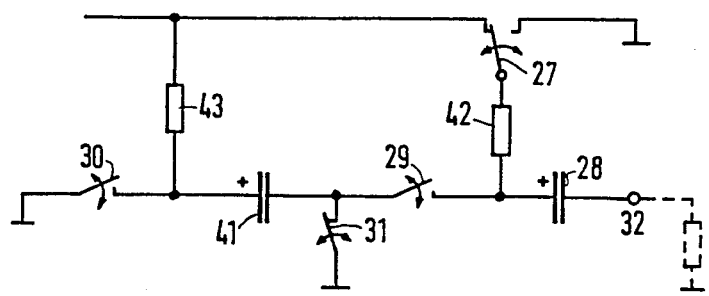
FIG. 5 is a circuit diagram for the output stage of the circuit shown in FIG. 4.

The output stage 26 schematically shown in FIG. 4 is shown in detail in FIG. 5. During normal operation, a switch 27 assumes the position shown in FIG. 5. During the charging phase of an output capacitor 28 (i.e., after a stimulation pulse has been emitted) the switches 29 and 30 are opened and the switch 31 is closed. For generating a stimulation pulse, the switches 29 and 30 are closed and the switch 31, which was previously closed, is opened. As a result, a stimulation pulse is generated at the output 32.

After emitting a stimulation pulse, the switch 30 is open, the switch 31 is closed, and the switch 29 is open. The switch 27 is in the left position as shown in the drawing. Through resistor 43, the capacitor 41 is continuously charged to a positive voltage. The capacitor 28 is also charged to a positive voltage through the resistor 42.

If a test mode is to be initiated, an appropriate signal is supplied to the transmitter/receiver 11 either via the coil 13 or by the application of a magnet which closes the switch 12. This causes the transmitter/receiver 11 to generate a signal to the mode register 2, which in turn generates a signal to the drive logic 8 indicating that a test is to be made. This in turn causes the drive logic 8 to move the switch 27 (FIG. 5) to the right position. When this is done, the circuit of FIG. 5 becomes a series circuit of the switch 27 in the right position, the register 42, the capacitor 28, the output terminal 32, and the patient load, which is indicated in FIG. 5 in dashed lines and which has a value of approximately 500 ohms.

A pulse will thus be produced with an amplitude having a value which is the operating voltage times the resistance value of the patient load divided by the sum of the resistance of the resistor 42 and the resistance of the patient load. A conventional operating voltage for pacemakers is 2.8 V, and as stated in the specification the amplitude of this pulse (the marking pulse) must be insufficent to stimulate the heart. The value of the resistor 42 is selecsted to achieve this result, the resistor 42, for example, having a value of 24 kohms. The marking pulse thus will have a value of 2.8. 500/24000+500, which is approximately equal to 60 mV. This value is not enough to stimulate the heart, but can be seen on an EKG recorder.

When a test mode for the battery is activated, both the drive logic 8 and the pacing logic 10 will control the output stage. The drive logic 8 controls the switch 27 as described above, and the logic 10 controls the other elements of FIG. 5. If a test mode is not activated, the switch 27 will always be in the left position as shown in FIG. 5, which means that the output logic (FIG. 5) will be exactly the same as the output logic for the pacing logic 10. The pacing logic 10 may, for example, be a microprocessor or hardware as in the commercially available model 668 chip. In the 668 chip, the pacing logic is accomplished using a binary rate multiplier (RBM) which is well known in the art. The drive logic 8, which is activated only in the test mode, may also consist of a BRM or a microprocessor.

As stated above, the pacemaker operates with a fixed frequency during the test mode. When the value in the battery test logic 21 is equal to the value of the time base generated by the clock generator 22, the switch 27 is briefly switched, for example for a duration of 1 ms. The components of the circuit of FIG. 5 are dimensioned such that the amplitude of the marking pulse generated is not sufficient to stimulate the heart.

Figure 6:
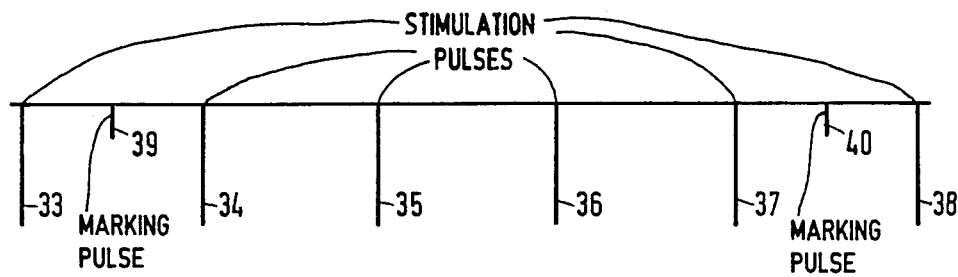
FIG. 6 is another type of pulse sequence for indicating the charge status of the battery generated in accordance with the principles of the present invention.

Another type of display mode which can be obtained in accordance with the principles of the present invention is shown in FIG. 6. In this embodiment, stimulation pulses 33 through 38 are supplied by the pacemaker during the test mode at a fixed frequency. Marking pulses, such as pulses 39 and 40, are generated at locations which are x times 100 ms after the respective preceding stimulation pulses 33 and 37, or y times 100 ms before the respective following stimulation pulses 34 and 38. The marking pulse 40 appears in the $n^{th}$ interval after the preceding marking pulse 33. In the example shown in FIG. 6, n=7 and x=y=4, indicating the remaining capacity of the battery is greater than 7.4 years.

Figure 7:
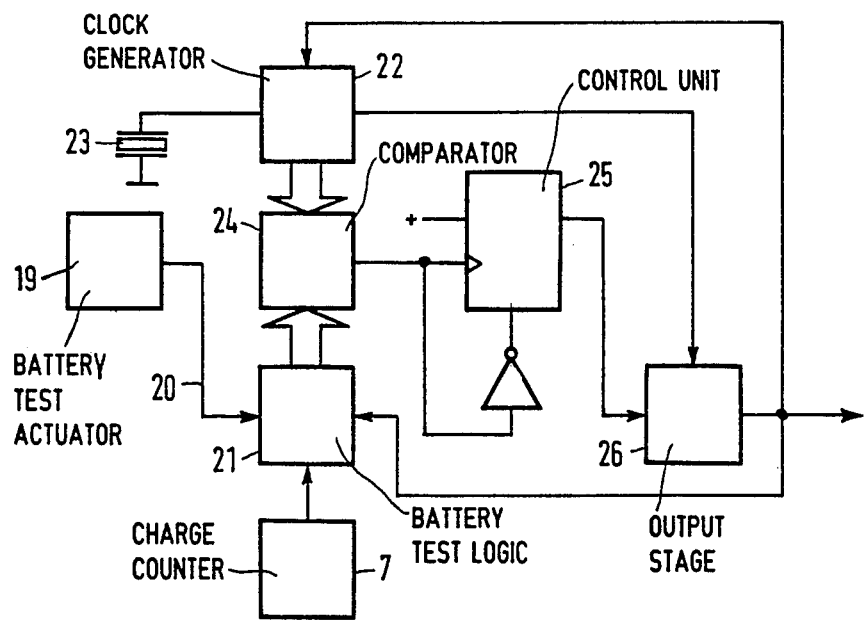
FIG. 7 is a schematic block diagram of a battery charge status test circuit constructed in accordance with the principles of the present invention for generating an output sequence a shown in FIG. 6.

The marking pulses 39 and 40 are generated by the circuit of FIG. 7, wherein components identical to the circuit of FIG. 4 are given the same reference symbols.

During a battery test, the value stored in the charge counter 7 is divided into a plurality of intervals which must be traversed before the marking pulse 40 is generated. When the correct interval arrives, the marking pulse 39 is first generated in the correct position in the interval. An output stage is already described in FIG. 5 is employed for this purpose. In this output stage, the switch 27 is always in the position indicated in the drawing when no battery test is being undertaken. During the charging phase of the output capacitor 28, switches 29 and 30 are opened and the switch 31 is closed. Capacitors 28 and 41 are charged by resistors 42 and 43.

A marking pulse is generated by closing the switches 29 and 30 and opening the switch 31. The output amplitude of the marking pulse is again selected such that stimulation of the heart does not occur, and the heart pacemaker frequency is fixed during the test mode. The value in the battery test logic 21 is compared to the time base. When the values are identical, i.e, when the correct time interval appears and the correct number of stimulation pulses have occurred since the marking pulse 39, the marking pulse 40 is generated by the switch 27. This marking pulse also does not stimulate the heart.

Therefore at every follow-up period at a hospital or other suitable facility, the external programmer 50, which communicates with the pacemaker, will read-out the actual parameter setting, the contents of the stimulation pulse counter 6, and the contents of the time register. From this data, it is possible to calculate the percentage of time since the last battery test which the pacemaker was actually pacing the heart. For example, assume the last test (or last re-programming) occurred on January 10. A follow-up is undertaken by the patient on February 15. The pacemaker was previously programmed to pace at a basic rate of 70 pulses per minute. If the pacemaker had been supplying stimulation pulses without interruption from January 10 until February 15, the content of the stimulation pulse counter 6 would be $3.63 \times 10^6$ stimulation pulses. Since the pacer will have been inhibited for a portion of this time, however, the content of the pulse counter 6 will be less than this value. If, for example, the content of the pulse counter 6 at the time of a test is $2.1 \times 10^6$, the pacemaker will have been supplying stimulation pulses 2.1/3.63=58% of the time. This value is this indicative of the charge status of the battery.

Although modifications and changes may be suggested by those skilled in the art it is the intention of the inventor to embody within the patent warranted hereon all changes and modifications as reasonably and properly come within the scope of his contribution to the art.

I claim as my invention:

1. A battery test circuit for a heart pacemaker which consumes charge from a battery and thereby changes a charge status of said battery, said pacemaker generating successive stimulation pulses, said battery test circuit comprising:
    a stimulation pulse counter for generating a signal corresponding to the number of said stimulation pulses;
    means for generating signals corresponding to operating values of said pacemaker;
    means for generating a time base signal indicative of elapsed time since a preceding battery test;
    logic means connected to said stimulation pulse counter, to said means for generating signals corresponding to said operating values, and to said means for generating a time base signal, said logic means calculating a value based on all of said signals corresponding to the consumed charge of said battery; and
    a charge counter memory connected to said logic means for storing values from said logic means generated since said preceding battery test, the content of said charge counter memory representing the present charge status of said battery.

2. A battery test circuit as claimed in claim 1, further comprising a transmitter/receiver receiving a signal for initiating and ceasing a battery test.

3. A battery test circuit as claimed in claim 2, wherein said transmitter/receiver includes means for sampling the stored value in said charge counter memory and means for transmitting a signal corresponding to the sampled stored value.

4. A circuit as claimed in claim 1, wherein said circuit has a size adapted for implantation as part of said heart pacemaker, and further comprising an external unit for programming and obtaining information from said circuit.

5. A circuit as claimed in claim 1, further comprising: means for generating at least one marking pulse; and means for mixing said marking pulse with said stimulation pulses connected to said charge counter memory, said means for mixing generating a mixed signal and including means for disposing the marking pulse in said mixed signal at a chronological position with respect to at least one of said stimulation pulses which corresponds to the charge status of said battery.

* * * * *